United States Patent [19]

Inoue et al.

[11] Patent Number: 4,524,017
[45] Date of Patent: Jun. 18, 1985

[54] DERIVATIVES OF NORBORNANES HAVING HYDROCARBON SIDE CHAINS AND PERFUME COMPOSITIONS CONTAINING THE SAME

[75] Inventors: Yoshiharu Inoue, Osaka; Fumio Tanimoto, Kyoto; Hisao Kitano, Osaka, all of Japan

[73] Assignee: Nippon Petrochemicals Co., Ltd., Tokyo, Japan

[21] Appl. No.: 351,993

[22] Filed: Feb. 24, 1982

[30] Foreign Application Priority Data

Feb. 28, 1981 [JP] Japan .................... 56-29188
Feb. 28, 1981 [JP] Japan .................... 56-29189
Aug. 22, 1981 [JP] Japan .................... 56-131743
Aug. 22, 1981 [JP] Japan .................... 56-131744

[51] Int. Cl.³ .............. A61K 7/46; C07C 47/445; C07C 47/347; C07C 33/14
[52] U.S. Cl. ............... 252/522 R; 568/820; 568/445
[58] Field of Search ............ 568/820, 445; 254/522 R

[56] References Cited

U.S. PATENT DOCUMENTS

| | | | |
|---|---|---|---|
| 3,860,635 | 1/1975 | Kitchens | 568/820 X |
| 4,128,509 | 12/1978 | Schleppnik | 568/820 X |
| 4,223,168 | 9/1980 | Light et al. | 568/820 X |
| 4,229,600 | 10/1980 | Kobayashi et al. | 568/820 |

Primary Examiner—Bernard Helfin

Attorney, Agent, or Firm—Hamilton, Brook, Smith & Reynolds

[57] ABSTRACT

Norbornane derivatives having hydrocarbon side chains, the processes for preparing the same and perfume compositions containing the same. The norbornane derivatives are represented by the following general formula (I)

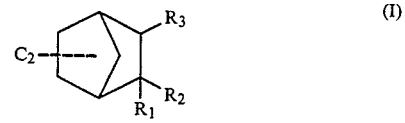

wherein $C_2$ is an ethyl group, an ethylidene group or a vinyl group each connected to 5 or 6 position of the norbornane ring, each of $R_1$ and $R_2$ is a hydrogen atom or a methyl group, and $R_3$ is a formyl group or a group represented by the following general formula (II)

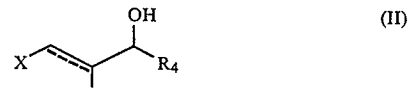

wherein $R_4$ is a methyl group, an ethyl group, a n-propyl group or an isopropyl group, and X is a carbon atom of the norbornane ring. The above norbornane derivatives give a wide variety of woody fragrances and are useful as components for various perfume products.

6 Claims, No Drawings

DERIVATIVES OF NORBORNANES HAVING HYDROCARBON SIDE CHAINS AND PERFUME COMPOSITIONS CONTAINING THE SAME

BACKGROUND OF THE INVENTION

1. Field of the Invention

This invention relates to derivatives of norbornanes, processes for preparing the same and perfume compositions containing the same. More particularly, the invention relates to novel derivatives of norbornanes having hydrocarbon side chains, especially, saturated or unsaturated hydrocarbons containing two carbon atoms, processes for preparing the same and perfume compositions containing the same.

2. Description of the Prior Art

A variety of synthetic perfume components have been prepared in order to make up for or to use in place of expensive natural perfume components. For example, compounds having norbornane bicyclo-[2,2,1]-heptane ring are proposed in several references.

U.S. Pat. No. 3,673,261 and No. 3,673,263 disclose 2-methyl-3-(5′-hydroxyalkenyl)-norbornanes. U.S. Pat. No. 3,748,344 discloses a process for preparing cyclic acetals of norbornane carboxyaldehydes. U.S. Pat. No. 3,860,635 discloses a process for preparing vinyl norbornanone. Further, disclosed in U.S. Pat. No. 4,076,853 are various kinds of alpha-allyl or methallyl-3,3-dimethyl-2-norbornyl methanols.

However, in connection with the specific norbornane derivatives having hydrocarbon side chains containing two carbon atoms of the present invention, no disclosure is found.

BRIEF SUMMARY OF THE INVENTION

The present invention is based upon the fact that the inventors found novel norbornane derivatives, processes for preparing the same and perfume compositions containing the same, as described below.

The object of the present invention is, therefore, to provide such a new finding.

The present invention relates to derivatives or norbornanes having hydrocarbon side chains, processes for preparing the same and perfume compositions containing the same. The norbornane derivatives of the invention are represented by the following general formula (I)

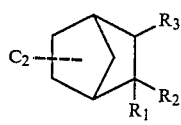

wherein $C_2$ is an ethyl group, an ethylidene group or a vinyl group each connected to 5 or 6 position of the norbornane ring, the dashed line connected to $C_2$ is a single bond when $C_2$ is an ethyl group or a vinyl group and a double bond when $C_2$ is an ethylidene group, each of $R_1$ and $R_2$ is a hydrogen atom or a methyl group, and $R_3$ is a formyl group or a group represented by the following general formula (II)

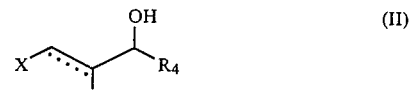

wherein $R_4$ is a methyl group, an ethyl group, a n-propyl group or an isopropyl group, the combination of a solid line with a dotted line indicates a single bond or a double bond, and X is a carbon atom of the norbornane ring.

According to the present invention, the norbornane derivatives represented by the foregoing general formula (I) can be prepared by hydrolyzing and decarboxylating glycidic esters represented by the following general formula (III) at temperatures in the range of 0° to 250° C.

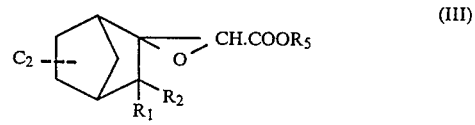

wherein $C_2$, dashed line, $R_1$ and $R_2$ are respectively the same as those in the foregoing general formula (I) and $R_5$ is a hydrocarbon group having 1 to 6 carbon atoms. Through this process, a norbornane derivative of formula (I) having a formyl group as $R_3$ can be prepared.

The inventors have found another method to prepare the norbornane derivative of formula (I) having a formyl group as $R_3$ by reacting 2-norbornene represented by the following general formula (IV) with carbon monoxide and hydrogen gas in the presence of a catalyst at temperature in the range of 30° to 300° C.

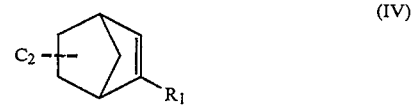

wherein $C_2$, dashed line and $R_1$ are respectively the same as those in the formula (I). The reaction product in this process has a hydrogen atom as $R_2$ and a formyl group as $R_3$ in the foregoing general formula (I).

Further, when $R_3$ is not a formyl group but a group represented by the foregoing general formula (II), the product obtained from any one of the above processes, that is, a norbornyl aldehyde, is reacted with ethyl alkyl ketone in the presence of an aldol condensation catalyst at temperatures in the range of 0° to 200° C. and thereafter the reaction product is subjected to dehydration and reduction, thereby obtaining the norbornane derivative of formula (I) having a group of formula (II) as $R_3$.

Also included in the present invention is perfume compositions containing the norbornane derivatives represented by the above-defined formula (I).

DETAILED DESCRIPTION OF THE INVENTION

The present invention will now be described in more detail.

As described above, the norbornane derivatives of the present invention are represented by the following general formula (I)

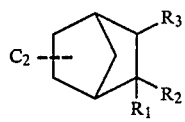

wherein C₂ is an ethyl group, an ethylidene group or a vinyl group each connected to 5 or 6 position of the norbornane ring, the dashed line connected to C₂ is a single bond when C₂ is an ethyl group or a vinyl group and a double bond when C₂ is an ethylidene group, each of R₁ and R₂ is a hydrogen atom or a methyl group, and R₃ is a formyl group or a group represented by the following general formula (II)

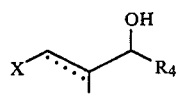

wherein R₄ is a methyl group, an ethyl group, a n-propyl group or an isopropyl group, the combination of a solid line with a dotted line indicates a single bond or a double bond, and X is a carbon atom of the norbornane ring.

The compounds included in the above norbornane derivatives represented by the general formula (I) are:
5- or 6-ethylnorbornyl-2-aldehyde,
5- or 6-ethylidenenorbornyl-2-aldehyde,
5- or 6-vinylnorbornyl-2-aldehyde,
their 3-methyl derivatives and 3,3-dimethyl derivatives, and
4-(5'- or 6'-ethylnorbornan-2'-yl)-3-methylbutan-2-ol,
4-(5'- or 6'-ethylidenenorbornan-2'-yl)-3-methylbutan-2-ol,
4-85'- or 6'-vinylnorbornan-2'-yl)-3-methylbutan-2-ol,
4-(5'- or 6'-ethylnorbornan-2'-yl)-3-methyl-3-buten-2-ol,
4-(5'- or 6'-ethylidenenorbornan-2'-yl)-3-methyl-3-buten-2-ol,
4-(5'- or 6'-vinylnorbornan-2'-yl)-3-methyl-3-buten-2-ol,
1-(5'- or 6'-ethylnorbornan-2'-yl)-2-methylpentan-3-ol,
1-(5'- or 6'-ethylidenenorbornan-2'-yl)-2-methylpentan-3-ol,
1-(5'- or 6'-vinylnorbornan-2'-yl)-2-methylpentan-3-ol,
1-(5'- or 6'-ethylnorbornan-2'-yl)-2-methyl-1-penten-3-ol,
1-(5'- or 6'-ethylidenenorbornan-2'-yl)-2-methyl-1-penten-3-ol,
1-(5'- or 6'-vinylnorbornan-2'-yl)-2-methyl-1-penten-3-ol,
1-(5'- or 6'-ethylnorbornan-2'-yl)-2,4-dimethylpentan-3-ol,
1-(5'- or 6'-ethylidenenorbornan-2'-yl)-2,4-dimethylpentan-3-ol,
1-(5'- or 6'-vinylnorbornan-2'-yl)-2,4-dimethylpentan-3-ol,
1-(5'- or 6'-ethylnorbornan-2'-yl)-2,4-dimethyl-1-penten-3-ol,
1-(5'- or 6'-ethylidenenorbornan-2'-yl)-2,4-dimethyl-1-penten-3-ol,
1-(5'- or 6'-vinylnorbornan-2'-yl)-2,4-dimethyl-1-penten-3-ol,
1-(5'- or 6'-ethylnorbornan-2'-yl)-2-methylhexan-3-ol,
1-(5'- or 6'-ethylidenenorbornan-2'-yl)-2-methylhexan-3-ol,
1-(5'- or 6'-vinylnorbornan-2'-yl)-2-methylhexan-3-ol,
1-(5'- or 6'-ethylnorbornan-2'-yl)-2-methyl-1-hexen-3-ol,
1-(5'- or 6'-ethylidenenorbornan-2'-yl)-2-methyl-1-hexen-3-ol,
1-(5'- or 6'-vinylnorbornan-2'-yl)-2-methyl-1-hexen-3-ol,
their 3'-methyl derivatives and 3',3'-dimethyl derivatives.

The above norbornane derivatives according to the present invention have woody odors as their fundamental note, and vary from fragrant tone to deep tone with their structures. They may be favorably formulated with not only woody notes but also floral, fougere, mossy, spicy, chypre, leather, tobacco, animal, citrus, resinous, green, aldehydic or the like to give various fragrant, perfumes and flavors.

Accordingly, the norbornane derivatives of the present invention are of great importance as bases for various perfume compositions, which may be employed to provide fragrance in perfumes, cosmetics, detergents, household products, toiletries, bleaches, antiperspirants, deodorants, aerosol products, bath preparation and the aromatic goods. They may also be applied widely to flavor components, artificial essential oil components, perfume extenders and the like.

One of the typical methods for preparing the norbornane derivatives according to the present invention is as follows: a glycidic ester represented by the following general formula (III) is hydrolyzed and decarboxylated at temperatures in the range of 0° to 250° C.

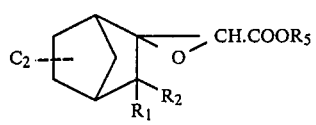

wherein the definitions for C₂, dashed line, R₁, R₂ and R₅ are the same as those previously defined.

Hydrolysis of the above glycidic ester may be carried out in an acidic aqueous solution or a basic aqueous solution. It is, however, generally carried out in a basic condition because the hydrolysis proceeds more easily. As the reaction medium, water and an alcohol, for example, a mixture of water and ethyl alcohol is employed. Used as basic materials are alkali metal hydroxides such as sodium hydroxide and potassium hydroxide, metal alcoholates such as sodium methylate, alkaline carbonates and anion exchange resins. The temperatures for hydrolysis should be in the range of 0° to 100° C.

The glycidic ester is hydrolyzed under a basic condition to afford, in general, the glycidic acid salt, which is converted into glycidic acid by adding a mineral acid such as hydrochloric acid and it is then subjected to decarboxylation at temperatures in the range of 0° to 250° C. When the decarboxylation is carried out at temperatures lower than 0° C., the reaction is difficult to proceed. On the other hand, when the reaction temperature is higher than 250° C., the decarboxylation is accompanied by side reactions such as decomposition and polymerization to a considerable extent. A preferable range of the decarboxylation temperature is 10° to 150° C. Heating during the decarboxylation may be continued until the evolution of carbon dioxide ceases. This heating time is generally 0.5 to 5 hours. Incidentally, the hydrocarbon group R₅ having more than 6 carbon atoms of the foregoing general formula (III) is not desirable because the decarboxylation becomes difficult.

After the above-described reaction, the reaction product is separated from the reaction mixture by means of suitable operations such as extraction or distillation and the reaction product is further purified to obtain the norbornane derivative of general formula (I) having a formyl group as the group $R_3$.

The glycidic esters represented by the foregoing general formula (III) can be prepared by reacting the norbornanone represented by the following general formula (V) with alkyl monohalogenoacetates such as alkyl chloroacetate and alkyl bromoacetate in the presence of a basic catalyst, permitting dehydrohalogenation

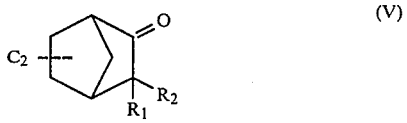

wherein $C_2$, dashed line, $R_1$ and $R_2$ are the same as those in formula (I). The alkyl groups of the alkyl monohalogenoacetates are exemplified by methyl, ethyl, propyl, isopropyl, butyl, sec-butyl, amyl, isoamyl, hexyl, 2-ethylhexyl and cyclohexyl groups.

In the above dehydrohalogenation, when the carbon atom number of the alkyl group of the alkyl monohalogenoacetate lies from 1 to 6, considerably smooth reaction can be accomplished, because the hydrolysis of the glycidic ester and subsequent decarboxylation can be easily performed. When the carbon atom number of the alkyl group of the alkyl monohalogenoacetate is 7 or more, the dehydrohalogenation, hydrolysis and decarboxylation require much time, which is economically disadvantageous from the industrial point of view. It is, therefore, preferable to use the alkyl monohalogenoacetate in which the alkyl group has 1 to 6 carbon atoms. Commercially available alkyl monohalogenoacetates are exemplified by methyl chloroacetate, ethyl chloroacetate, isopropyl chloroacetate and ethylene bis(chloroacetate).

The norbornane derivatives of formula (I) having a formyl group as $R_3$ of the same formula may be prepared by an alternative method. That is, the norbornene represented by the following general formula (IV) is reacted with carbon monoxide and hydrogen gas in the presence of a catalyst at temperatures in the range of 30° to 300° C.

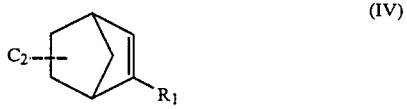

Exemplified as compounds of the above formula (IV) are 5-ethyl-2-norbornene, 5- or 6-ethyl-3-methyl-2-norbornene, 5-vinyl-2-norbornene, 5- or 6-vinyl-3-methyl-2-norbornene, 5-ethylidene-2-norbornene and 5- or 6-ethylidene-3-methyl-2-norbornene.

The above reaction is represented by the following reaction formula:

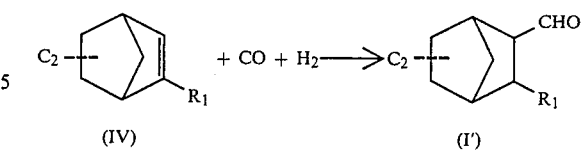

As the products in the above reaction, a norbornane derivative having a formyl group at the neighboring position of $R_1$ in the norbornane ring and other by-product are also produced in addition to the norbornane derivative represented by the foregoing formula (I') having a formyl group as $R_3$. Accordingly, it is of great importance to select the catalyst in order to obtain the maximum yield of the norbornyl-2-aldehyde of formula (I'), the aimed product of the invention.

In accordance with the results of many experiments, it has been found that transition metal compounds can be used in order to complete the above reaction and, especially, the compounds of group VIII elements of the periodic table are advantageously employed.

Among the group VIII metal compounds, those of cobalt, rhodium, iridium, ruthenium and platinum are preferable. When the complexes of carbonyl compounds of these metals are used, it is, of course, important to give consideration to the kind of ligands to be coordinated in order to improve the selectivity in the reaction, in which electron donating properties and steric factors should also be taken into account.

Some of metal carbonyl compounds are commercially available, however, they can be prepared before use by reacting activated metal powder or other metal compounds with carbon monoxide. In order to improve catalytic activity, the following compounds may be coordinated with these carbonyl complexes or added to the reaction system. There are tertiary amines, phosphines and phosphites as such ligands. Especially, in the hydroformylation of the present invention, adduct complexes of tertiary phosphines such as tributyl phosphine and triphenyl phosphine are quite useful for improving the selectivity of the aimed products. Among the above-mentioned metal compounds, cobalt compounds and rhodium compounds are preferable. They can be used singly or in combination with other metal compounds as a promoter.

When the above metal compounds are used, reaction temperatures may be in the range of 30° to 300° C., more preferably 50° to 250° C. Reaction pressures are generally in the range of 1 to 450 kg/cm².

The molar ratio of carbon monoxide to hydrogen that are introduced into the reaction system can be varied within the range of 1:1 to 1:4, however, the ratio of 1:1 is commonly used.

The hydroformylation is usually carried out in a liquid phase using a reaction medium. Exemplified as such reaction media are one or a mixture of saturated hydrocarbons, aromatic hydrocarbons such as benzene, ethers, alcohols, esters, sulfolanes, water and reaction materials themselves.

In the hydroformylation procedure, the above 2-norbornene is charged together with carbon monoxide, hydrogen gas and the reaction medium into an autoclave and the reaction is carried out in the presence of a catalyst by heating at a predetermined temperature. After the reaction is completed, an excess of carbon monoxide and hydrogen gas are purged from the vessel and the catalyst is removed or decomposed through an appropriate method. After that, the reaction product is further treated by, for example, fractional distillation to obtain the aimed norbornane derivative.

When the group $C_2$ is an ethylidene group or a vinyl group in the foregoing glycidic ester of general formula (III) or the norbornane of general formula (IV), the corresponding norbornane derivative of general formula (I) having an ethylidene group or a vinyl group as $C_2$ will be obtained. In the case where a norbornane derivative of general formula (I) having an ethyl group as $C_2$ is desired as the final product, the group $C_2$ of the above reaction product is further subjected to partial hydrogenation.

In this partial hydrogenation, the formyl group is not reduced but the ethylidene group or vinyl group is selectively hydrogenated into an ethyl group. This reaction may be carried out by catalytic hydrogenation or by using a reducing agent. As catalysts for the catalytic hydrogenation, the group VIII metals of the periodic table such as palladium, platinum, rhodium, and their compounds are preferably used. These catalysts may be deposited on a carrier such as a charcoal. The reaction pressure is in the range of ordinary pressure to 50 kg/cm$^2$ of hydrogen and the reaction temperature is in the range of $-10$ to 200° C. As reaction media, alcohols such as ethyl alcohol, saturated hydrocarbons such as hexane, aromatic hydrocarbons such as benzene, and esters such as ethyl acetae may be used.

When the partial hydrogenation is carried out by using a nickel catalyst or a reducing agent such as diimide, the formyl group of ethylidene- or vinylnorbornyl-2-aldehyde is protected by converting it into acetal. After the hydrogenation, the reaction product is subjected to acidic hydrolysis to regenerate the aldehyde.

It is known that ethylnorbornyl-2-aldehyde is obtained through the Diels-Alder reaction between an alkylcyclopentadiene and acrolein. However, in this case, many kinds of the Diels-Alder reaction by-products are formed and the yield of the aimed product is not good. Therefore, this method may be disadvantageous in a commercial production.

When the final product of the foregoing general formula (I) has a group of $R_3$ other than a formyl group and the group $R_3$ is represented by the foregoing general formula (II), the final product is prepared by reacting the above-described norbornyl-2-aldehydes with ethyl alkyl ketones in the presence of an aldol condensation catalyst at temperatures in the range of 0° to 200° C., which is followed by dehydration and reduction.

The above-mentioned ethyl alkyl ketones used in the aldol condensation with the above norbornyl-2-aldehyde are exemplified by ethyl lower-alkyl ketones such as methyl ethyl ketone, diethyl ketone, ethyl propyl ketone and ethyl isopropyl ketone.

In the aldol condensation, acidic and basic substances are used as catalysts. The acidic catalysts may include inorganic acids such as sulfuric acid, hydrochloric acid, phosphoric acid and hydrobromic acid, Lewis acids such as boron trifluoride, and organic acids such as benzene sulfonic acid, trifluoromethane sulfonic acid, toluene sulfonic acid, naphthalene sulfonic acid, trifluoroacetic acid, trichloroacetic acid and sulfamic acid. The basic catalysts may include metal hydroxides such as lithium hydroxide, sodium hydroxide, potassium hydroxide, barium hydroxide and calcium hydroxide, metal alkoxides such as lithium methylate, sodium methylate, sodium ethylate, potassium methylate, aluminum isopropoxide and potassium tert-butoxide, and weak basic compounds such as sodium carbonate, potassium carbonate, potassium acetate and potassium fluoride. Further exemplified as the basic catalysts are sodium hydride, lithium hydride, potassium hydride, lithium amide, sodium amide, potassium amide, tertiary amines, quaternary ammonium salts, active methylene alkali compounds, alkali fluorides, alkali metal oxides, alkaline earth metal oxides and cyclic amines. Among them, alkali hydroxides, alkali carbonates, alkali alkoxides, alkali amides, tertiary amines, cyclic amines and alkali salts of weak organic acids are important for industrial production.

The temperature of the aldol condensation is in the range of 0° to 200° C., preferably 50° to 150° C. and the pressure may be any of the atmospheric pressure, elevated pressures or reduced pressures as far as the reaction temperature is maintained within a predetermined range.

The reaction may be carried out without any reaction medium, but reaction media can, of course, be used so as to bring reaction materials into sufficient contact with catalyst and to make reaction temperature uniform. Used as such reaction media are an excess amount of ketones themselves, alcohols, water, saturated hydrocarbons, ethers, and halogenated hydrocarbons. They can be employed singly or in combination of two kinds or more.

In this process, the hydrogenation is performed after the aldol condensation of norbornyl-2-aldehyde and ethyl alkyl ketone, however, when reaction conditions are properly selected, the aldol condensation is generally followed by spontaneous dehydration. In this case, there is no need for the dehydration process. However, according to selected reaction conditions, for example, when the temperature of condensation is relatively low, the dehydration may be readily carried out by heating with or without adding a dehydrating agent.

Through the above-described processes, the ketones represented by the general formulae (VI) and (VII) in the following reaction scheme are obtained. Shown in this reaction scheme are the cases where norbornyl-2-aldehydes of general formula (I''), that is, the norbornane derivatives of general formula (I) having hydrogen atoms as $R_1$ and $R_2$, are reacted with diethyl ketone to produce reaction products of general formulae (VI) and (VII), which are then reduced.

In the reaction scheme, the symbol $C_2'$ indicates an ethylidene group or a vinyl group. As shown in the reaction scheme, the norbornane derivatives of the present invention as represented by the general formulae (IX), (X), (XI) and (XII) can be prepared by reducing the ketones of general formulae (VI) and (VII).

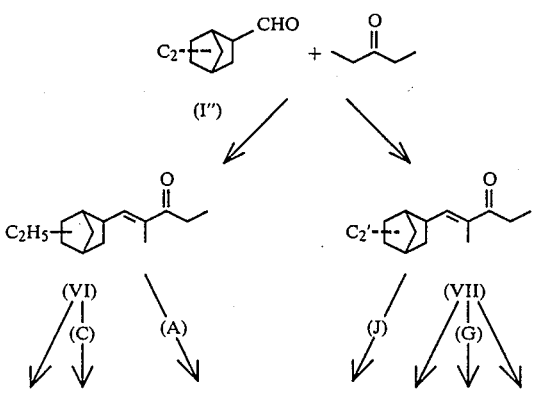

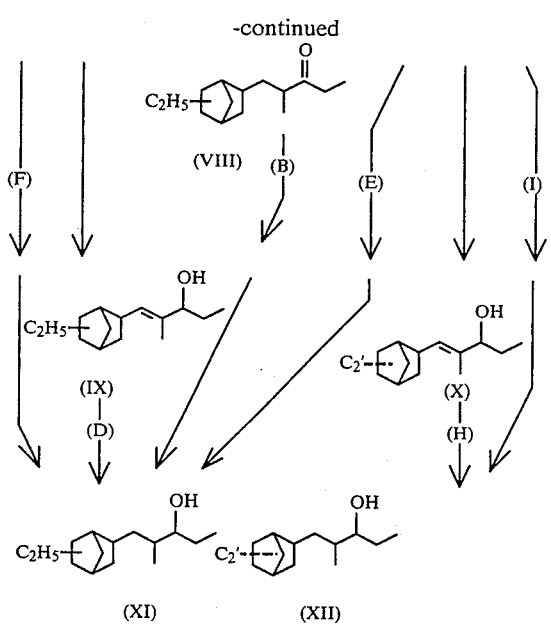

In this reaction scheme, it should be noted that only the carbonyl groups are selectively reduced into the hydoxy groups in steps (B), (C), (G) and (H).

In these steps, metal hydrides, aluminum alkoxides and alcohols, or alkoxides of alkali metals or alkaline earth metals and alcohols are advantageously used as reducing agents. Further, the reduction may be carried out by catalytic hydrogenation in the presence of a suitable catalyst under mild conditions, or it may also be carried out by an electrolytic reduction.

Exemplified as the above-mentioned metal hydrides are sodium borohydride, lithium borohydride, lithium aluminum hydride, sodium aluminum hydride, aluminum hydride complex, lithium hydride, sodium hydride, calcium hydride and bis(methoxyethyl)aluminum sodium hydride. An example of the combination of alcohol and aluminum alkoxide is a combination of isopropyl alcohol and aluminum isopropoxide.

As the media for reduction using these reducing agents, one or a mixture of two or more of alcohols such as methyl alcohol, ethyl alcohol and isopropyl alcohol, ethers such as dioxane, diethyl ether, ethylene glycol dimethyl ether and tetrahydrofuran, saturated aliphatic hydrocarbons, aromatic solvents such as toluene, and aliphatic alkyl esters may be used.

The temperature of reduction is generally in the range of 0° to 150° C. After the reduction, unreacted materials and reaction medium are separated to collect the organic layer containing the aimed product, which is further subjected to purification such as fractional distillation to obtain the final product.

In the steps of (A), (D), (H) and (J) in the foregoing reaction scheme, the carbon-carbon double bonds are reduced while carbonyl groups and hydroxy groups remain uneffected. Therefore, this reduction is carried out by catalytic hydrogenation under mild conditions. Exemplified as preferable catalysts for this catalytic hydrogenation are group VIII metals of the periodic table such as nickel, cobalt, ruthenium, rhodium or platinum. They may be conveniently used on carriers such as barium sulfate, alumina or calcium carbonate. The pressure of this catalytic hydrogenation may be in the range of ordinary pressure to 10 kg/cm$^2$ and the reaction temperature may be in the range of 0° to 150° C.

In the reducing steps (E) and (F) of the foregoing reaction scheme, the reduction of carbon-carbon double bonds into single bonds and the reduction of carbonyl groups into hydroxy groups are simultaneously carried out by the catalytic hydrogenation. In this case, suitable conditions must be selected to avoid the hydrogenolysis of formed hydroxy groups. In these steps, catalysts of nickel, cobalt, platinum, copper chromite, ruthenium and rhodium are generally used. As the catalyst carrier of them, activated carbon or alumina is employed. Reaction media are not necessarily used in the reaction. If, however, they are used, alcohols such as ethyl alcohol and saturated cyclic hydrocarbons such as cyclohexane are preferable. The reaction temperatures of the catalytic hydrogenation is in the range of 30° to 300° C. and the reaction pressure is in the range of 2 to 300 kg/cm$^2$.

In the reducing step of (I) represented in the foregoing reaction scheme, the carbon-carbon double bonds conjugated with the carbonyl group are selectively reduced to form the unconjugated ketone, which is further reduced to the hydroxy group by the same method as the step (G).

This selective reaction is performed by adding a solution of the unsaturated ketone in ethers such as diethyl ether, tetrahydrofran, dioxane and diethyleneglycol dimethylether and one equivalent or more of a proton donor such as ethanol or tert-butyl alcohol to a solution containing more than two equivalents of sodium or lithium in liquid ammonia or alkyl amines such as ethylamine, n-propylamine and isopropylamine.

The reaction temperature of this partial reduction is ranging from −70° to 50° C., preferably −30° to 20° C. The unconjugated ketone thus obtained is subjected to further reduction to form the alcohol in the same manner as the stop (G).

Through the above-described processes, the norbornane derivatives represented by the foregoing general formula (I) can be prepared.

The present invention is now further described with reference to several examples.

EXAMPLE 1

Preparation of 5- or 6-ethylnorbornyl-2-aldehyde

A mixture of 2.5 g (0.011 mole) of glycidic esters represented by the following formulae was dissolved in 10 ml of methyl alcohol.

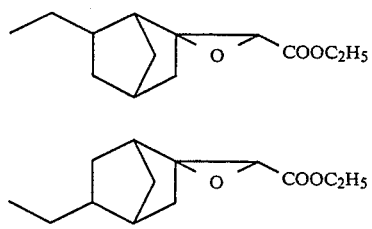

To the solution was added 2.5 g of 28% sodium methylate solution in methanol at a temperature below 20° C. After that, 0.3 ml of water was added to the mixture and hydrolysis was carried out by boiling the reaction mixture for 4 hours with stirring.

To the reaction mixture thus obtained were added 2 ml of concentrated hydrochloric acid and 6 ml of water and decarboxylation was carried out with stirring the mixture for 3 hours at 25° to 30° C. After the reaction, the reaction mixture was neutralized, rinsed with water and dried, and the solvents were distilled off. After that, 1.0 g of the 5- or 6-ethylnorbornyl-2-aldehyde was obtained in a yield of 60%. The boiling point of the product was 52°–53° C./3.0 mmHg.

Other analytical data on the reaction product will be shown as follows:

IR (Infrared spectrum analysis): C—H stretching vibration of the aldehyde at 2,730 cm$^{-1}$ and C=O stretching vibration of the aldehyde at 1,725 cm$^{-1}$ were observed.

NMR (Nuclear magnetic resonance): 0.3τ (doublet, 1H); 6.8–9.3τ (multiplet, 15H).

| Elemental Analysis: (as $C_{10}H_{16}O$) | | |
|---|---|---|
| | C (%) | H (%) |
| Calculated: | 78.9 | 10.5 |
| Found: | 78.6 | 10.6 |

EXAMPLE 2

Preparation of 5- or 6-vinylnorbornyl-2-aldehyde

A mixture of 2.5 g (0.011 mole) of glycidic esters represented by the following formulae was dissolved in 10 ml of 99.5% ethyl alcohol.

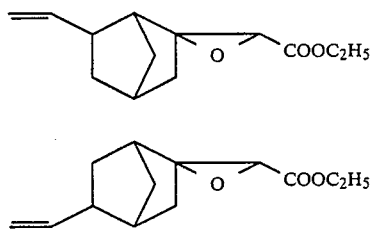

To the solution was added 2.5 g of 28% sodium methylate solution in methyl alcohol at a temperature below 20° C. After that, 0.3 ml of water was added to the mixture and the glycidic esters were hydrolyzed by heating the reaction mixture to about 70° C. for 3 hours with stirring.

To the reaction mixture thus obtained were added 1.2 ml of concentrated hydrochloric acid and 5.7 ml of water and decarboxylation was then carried out by refluxing the mixture for 3 hours. After this reaction, the reaction mixture was neutralized, rinsed with water and dried, and the solvent was distilled off. After that, 0.9 g of the 5- or 6-vinylnorbornyl-2-aldehyde was obtained in a yield of 54.5% by distillation under reduced pressure. The boiling point of the obtained product was 67° C./3.0 mmHg.

IR: C—H stretching vibration of vinyl groups at 3,050 cm$^{-1}$, C=C stretching vibration of vinyl groups at 1,630 cm$^{-1}$, C—H stretching vibration of the aldehyde at 2,730 cm$^{-1}$, and C=O stretching vibration of the aldehyde at 1,725 cm$^{-1}$ were observed.

NMR: 0.3τ (singlet, 1H); 4.1τ (multiplet, 1H); 4.8τ (multiplet, 2H); 6.5–9.0τ (multiplet, 10H).

| Elemental Analysis: (as $C_{10}H_{14}O$) | | |
|---|---|---|
| | C (%) | H (%) |
| Calculated: | 80.0 | 9.3 |
| Found: | 79.8 | 9.4 |

EXAMPLE 3

Preparation of 5- or 6-ethylidenenorbornyl-2-aldehyde

A mixture of 10.0 g (0.011 mole) of glycidic esters represented by the following formulae was dissolved in 50 ml of 99.5% ethyl alcohol.

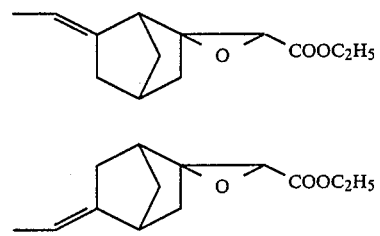

Hydrolysis and decaroxylation were carried out in a manner similar to the foregoing Example 2 to obtain 3.2 g of 5- or 6-ethylidenenorbonyl-2-aldehyde in a yield of 48%. The boiling point of the obtained product was 84°–87° C./10 mmHg.

IR: C—H stretching vibration of the aldehyde at 2,710 cm$^{-1}$, C=O stretching vibration of the aldehyde at 1,725 cm$^{-1}$, C—H stretching vibration of ethylidene groups at 3,009 cm$^{-1}$ and C=C stretching vibration of ethylidene groups at 1,665 cm$^{-1}$ were observed.

NMR: 0.3τ (singlet, 1H); 4.4–4.8τ (multiplet, 1H); 8.4τ (doublet, 3H); 6.5–9.1τ (multiplet, 9H).

| Elemental Analysis: (as $C_{10}H_{14}O$) | | |
|---|---|---|
| | C (%) | H (%) |
| Calculated: | 80.0 | 9.3 |
| Found: | 79.7 | 9.1 |

EXAMPLE 4

Preparation of 3-methyl-5- or 6-ethylnorbornyl-2-aldehyde

In place of the glycidic esters used in Example 1, 0.011 mole of a mixture of the glycidic esters represented by the following two formulae was used. This mixture was treated in a manner similar to Example 1.

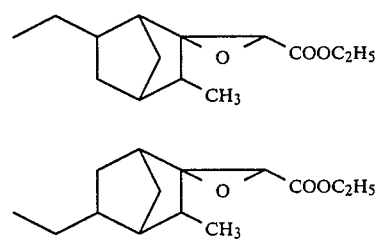

As a result, 3-methyl-5- or 6-ethylnorbornyl-2-aldehyde was obtained in a yield of 55%. The boiling point of this product was 48°–51° C./2.0 mmHg.

IR: C—H stretching vibration of the aldehyde at 2,730 cm$^{-1}$, and C=O stretching vibration of the aldehyde at 1,725 cm$^{-1}$ were observed.

NMR: 0.3τ (doublet, 1H); 6.5–9.0τ (multiplet, 14H); 9.1τ (doublet, 3H).

| Elemental Analysis: (as C$_{11}$H$_{18}$O) | | |
|---|---|---|
| | C (%) | H (%) |
| Calculated: | 79.5 | 10.8 |
| Found: | 79.0 | 10.6 |

EXAMPLE 5

Preparation of 3-methyl-5- or 6-vinylnorbornyl-2-aldehyde

In place of the glycidic esters used in Example 2, 0.011 mole of a mixture of the glycidic esters represented by the following two formulae was used. This mixture was treated in a like manner as Example 2.

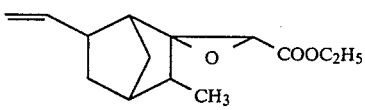

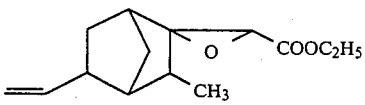

As a result, 3-methyl-5- or 6-vinylnorbornyl-2-aldehyde was obtained in a yield of 52.2%. The boiling point of this product was 55°–56° C./2.0 mmHg.

IR: C—H stretching vibration of vinyl groups at 3,050 cm$^{-1}$, C=C stretching vibration of vinyl groups at 1,630 cm$^{-1}$, C—H stretching vibration of the aldehyde at 2,730 cm$^{-1}$ and C=O stretching vibration of the aldehyde at 1,725 cm$^{-1}$ were observed.

NMR: 0.3τ (singlet, 1H); 4.1τ (multiplet, 1H); 4.8τ (multiplet, 2H); 6.5–9.0τ (multiplet, 9H); 9.1τ (doublet, 3H).

| Elemental Analysis: (as C$_{11}$H$_{16}$O) | | |
|---|---|---|
| | C (%) | H (%) |
| Calculated: | 80.5 | 9.8 |
| Found: | 80.2 | 9.5 |

EXAMPLE 6

Preparation of 3,3-dimethyl-5- or 6-ethylidenenorbornyl-2-aldehyde

In place of the glycidic esters used in Example 3, 0.044 mole of a mixture of the glicidic esters represented by the following two formulae was used. This mixture was treated in a like manner as Example 3.

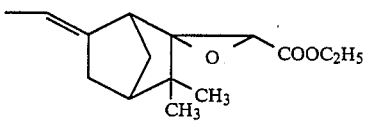

-continued

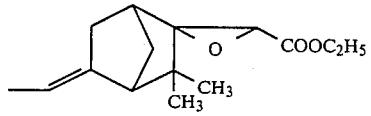

As a result, 3,3-dimethyl-5- or 6-ethylidenenorbornyl-2-aldehyde was obtained in a yield of 60.3%. The boiling point of this product was 66°–69° C./3 mmHg.

IR: C—H stretching vibration of ethylidene groups at 3,050 cm$^{-1}$, C=C stretching vibration of ethylidene groups at 1,675 cm$^{-1}$, C—H stretching vibration of the aldehyde at 2,725 cm$^{-1}$ and C=O stretching vibration of the aldehyde at 1,730 cm$^{-1}$ were observed.

NMR: 0.5τ (singlet, 1H); 4.5τ (multiplet, 1H); 6.7–9.0τ (multiplet, 7H); 8.5τ (doublet, 3H); 8.9τ (doublet, 6H).

| Elemental Analysis: (as C$_{12}$H$_{18}$O) | | |
|---|---|---|
| | C (%) | H (%) |
| Calculated: | 80.9 | 10.1 |
| Found: | 81.1 | 9.8 |

EXAMPLE 7-I

Preparation of 5- or 6-ethylnorbornyl-2-aldehyde

In a 200 ml autoclave was placed 5.0 g (0.033 mole) of 5- or 6-vinylnorbornyl-2-aldehyde, 100 ml of ethyl alcohol, and 0.2 g of 5% palladium-carbon catalyst and the autoclave was then closed tightly. Then, degasification and nitrogen gas displacement were repeated twice, the reaction was performed for one hour at room temperature with feeding hydrogen gas under pressure of 3 kg/cm$^2$. After the reaction was completed, the catalyst was removed by filtration from the reaction mixture and ethyl alcohol was recovered from the filtrate. The residue was distilled under reduced pressure to obtain 4.6 g of 5- or 6-ethylnorbornyl-2-aldehyde in a yield of 91%.

The physical properties and analytical results of the compound thus obtained were all the same as those of the reaction product in Example 1.

EXAMPLE 7-II

Preparation of 3-methyl-5- or 6-ethylnorbornyl-2-aldehyde

In place of 5- or 6-vinylnorbornyl-2-aldehyde used as a starting material in Example 7-I, 5.0 g (0.030 mole) of 3-methyl-5- or 6-ethylidenenorbornyl-2-aldehyde was used, and it was treated in a like manner as Example 7-I.

As a result, the aimed 3-methyl-5- or 6-ethylnorbornyl-2-aldehyde was obtained in a yield of 90%. The physical properties and analytical results of this product were all the same as those of the reaction product is Example 4.

EXAMPLES 8 TO 25

In these Examples 8 to 25, the preparation of norbornyl-2-aldehydes having hydrocarbon side chains of the present invention were carried out through hydroformylation using carbon monoxide and hydrogen gas.

In these Examples, each norbornene, reaction medium and catalyst indicated in the following Table 1 were fed into a 500 ml autoclave and synthesis gas (CO/H$_2$=1/1) was then charged under an elevated pressure. The reaction mixture in the autoclave was allowed to react under the conditions of pressure, temperature and time shown in Table 1. After the reaction was completed, the reaction mixture was cooled and excess unreacted gas was purged from the vessel. After treating the contents in the autoclave with oxygen and hydrochloric acid, the organic layer was separated from the catalyst. After the organic layer was washed with water and dried, the reaction medium was recovered and the residue was then subjected to distillation under reduced pressure. The obtained fraction was further purified by fractional distillation to obtain a main fraction.

In connection with the main fraction, IR and NMR spectrum analysis and elemental analysis were performed and the yield of the main fraction was also determined. The analytical data were compared with those in Examples 1 to 7-II in order to identify the structures of the products.

The results of these Examples 8 to 25 are also shown in the following Table 1.

TABLE 1

| Ex. No. | Starting Norbornene (mol.) | Reaction Medium (ml.) | Catalyst (mmol.) | Pres. (Kg/cm$^2$) | Temp. (°C.) | Time (hr.) | Reaction Product | Yield (%) |
|---|---|---|---|---|---|---|---|---|
| 8 | 5-Ethyl-norbornene-2 (0.1) | n-Heptane (200) | $Rh_4(CO)_{12}$ (2) | 50 | 120 | 15 | 5- or 6-Ethyl-norbornyl-2-aldehyde | 72 |
| 9 | 5-Ethyl-norbornene-2 (0.1) | Benzene (200) | $PhCCo_8(CO)_9$ (4) | 120 | 90 | 20 | 5- or 6-Ethyl-norbornyl-2-aldehyde | 72 |
| 10 | 5-Ethyl-norbornene-2 (0.1) | Tetrahydrofuran (200) | $Co_2(CO)_8$ (8) | 100 | 110 | 15 | 5- or 6-Ethyl-norbornyl-2-aldehyde | 70 |
| 11 | 5-Ethyl-norbornene-2 (0.1) | Ethanol (150) | Cobalt octylate (10) | 120 | 110 | 12 | 5- or 6-Ethyl-norbornyl-2-aldehyde | 64 |
| 12 | 5-Ethyl-norbornene-2 (0.1) | Dioxane (200) | $Co_2(CO)_8$ (8) | 80 | 80 | 15 | 5- or 6-Ethyl-norbornyl-2-aldehyde | 75 |
| 13 | 5-Ethyl-norbornene-2 (0.1) | Glycol dimethyl ether (200) | $CH_3CCo_3(CO)_9$ (4) | 95 | 110 | 10 | 5- or 6-Ethyl-norbornyl-2-aldehyde | 72 |
| 14 | 5-Ethyl-norbornene-2 (0.1) | n-Pentane (180) | $HCo(CO)_3$—$P(n-C_4H_9)_3$ (8) | 90 | 70 | 10 | 5- or 6-Ethyl-norbornyl-2-aldehyde | 78 |
| 15 | 5-Vinyl-norbornene-2 (0.1) | Hexane (200) | Activated $Ru(OH)_3$ (4) | 150 | 150 | 10 | 5- or 6-Vinyl-norbornyl-2-aldehyde | 38 |
| 16 | 5-Vinyl-norbornene-2 (0.1) | Benzene (180) | $IrCl(CO)$—$(Ph_3P)_2$ (20) | 130 | 80 | 24 | 5- or 6-Vinyl-norbornyl-2-aldehyde | 37 |
| 17 | 5-Vinyl-norbornene-2- (0.1) | Dioxane (180) | $Co_2(CO)_8$ (10) | 100 | 140 | 16 | 5- or 6-Vinyl-norbornyl-2-aldehyde | 43 |
| 18 | 5-Vinyl-norbornene-2 (0.1) | Ethanol (50) Dioxane (180) | Cobalt naphthenate (15) | 150 | 150 | 10 | 5- or 6-Vinyl-norbornyl-2-aldehyde | 41 |
| 19 | 5-Ethylidene-norbornene-2 (0.1) | γ-Butyrolactone (150) | $Co_2(CO)_8$ (10) | 100 | 140 | 16 | 5- or 6-Ethylidenenorbornyl-2-aldehyde | 44 |
| 20 | 5-Ethylidene-norbornene-2 (0.1) | Glycol dimethyl ether (200) | $HRhCO(PPh_3)_3$ (3) | 50 | 100 | 18 | 5- or 6-Ethylidenenorbornyl-2-aldehyde | 65 |
| 21 | 5-Ethylidene-norbornene-2 (0.1) | Hexane (200) | $HCo(CO)_3$—$P(n-C_4H_9)_3$ (15) | 80 | 80 | 15 | 5- or 6-Ethylidenenorbornyl-2-aldehyde | 59 |
| 22 | 5- or 6-Ethyl-3-methyl-norbornene-2 (0.1) | Benzene (200) | Activated $Rh(OH)_3$ (5) | 77 | 120 | 15 | 5- or 6-Ethyl-3-methyl-norbornyl-2-aldehyde | 65 |
| 23 | 5- or 6-Ethyl-3-methyl-norbornene-2 (0.1) | n-Hexane (170) | $HCo(CO)_3PPh_3$ (8) | 85 | 90 | 17 | 5- or 6-Ethyl-3-methyl-norbornyl-2-aldehyde | 79 |
| 24 | 5- or 6-Ethylidene-3-methyl-norbornene-2 (0.1) | Octane (180) | $Rh_4(CO)_{12}$ (3) | 90 | 100 | 8 | 5- or 6-Ethylidene-3-methyl-norbornyl-2-aldehyde | 46 |
| 25 | 5- or 6-Vinyl-3-methyl-norbornene-2 (0.1) | Benzene (240) | $PtH(SnCl_2)$—$(PPh_3)_2$ (15) | 105 | 100 | 20 | 5- or 6-Vinyl-3-methyl-norbornyl-2-aldehyde | 28 |

Note:
Symbol "Ph" in Catalyst means "phenyl group"

In the Examples of Table 1, catalysts were as uniformly dispersed or dissolved as possible into the reaction mixture. In the case of Example 20, the use of 15 mmole of 10% chloro-rhodium-carbonyl complex RhCl(CO)$_2$P(C$_6$H$_5$)$_2$ on silica powder, as a catalyst, gave almost the same result. It was observed that the yield of the aimed product is generally improved when the complex with phosphine ligand is used.

In Examples 10 and 19, even when cobalt hydrocarbonyl HCo(CO)$_4$ was used in place of the cobalt carbonyl Co$_2$(CO)$_8$, almost the same result was obtained. Further, in Examples 22 and 24, when rhodium carbonyl acetylacetonate was used in place of activated rhodium hydroxide Rh(OH)$_3$ or rhodium carbonyl Rh$_4$(CO)$_{12}$, almost the same results were obtained.

Furthermore, when palladium hydroxide Pd(OH)$_2$, nickel carbonyl Ni(CO)$_4$, nickel acetylacetonate Ni(C$_5$H$_7$O)$_2$ or iron carbonyl Fe(CO)$_5$ was used as a catalyst, the yield of the aimed product was decreased. Comparison of the results of many other experiments leads to the fact that cobalt and rhodium compounds are most preferable among group VIII metals of periodic table. Iridium and ruthenium compounds are also useful to some extent.

EXAMPLE 26

Preparation of 1-(5'- or 6'-ethylnorbornan-2'-yl)-2-methylpentan-3-ol

Diethyl ketone, 32 g (0.37 mole) was dissolved in 150 ml of methyl alcohol and 5 g of 40% sodium hydroxide aqueous solution was further added thereto. To the mixture, 21 g (0.14 mole) of a mixture of 5-vinylnorbornyl-2-aldehyde and 6-vinylnorbornyl-2-aldehyde was slowly added under reflux.

The aldol condensation was carried out by heating and refluxing this mixture for about 2 hours. In this reaction, since dehydration occurred simultaneously, no dehydration was needed. The reaction mixture was distilled under reduced pressure to give α,β-unsaturated ketone in a yield of 59%. With regard to this product, the existence of the carbonyl groups of the α,β-unsaturated ketone was confirmed by IR and NMR analysis, which indicated that the aldol concentration and subsequent dehydration were completed.

Then, 8.0 g (0.037 mole) of this α,β-unsaturated ketone, 200 ml of ethyl alcohol and 0.3 g of 5% palladium-carbon powder were placed in a 1 liter autoclave. After closing the autoclave, the contents were allowed to react under hydrogen pressure of 3 kg/cm$^2$ at room temperature for 2 hours. Then the catalyst was removed from the reaction mixture and ethyl alcohol was distilled off. The residue was distilled under reduced pressure to afford a saturated ketone, in which the yield was 60.9% and the boiling point thereof was 101°–102° C./1.5 mmHg.

According to the analysis of this product, IR spectrum (neat) indicated the existence of the carbonyl group and NMR spectrum (CCl$_4$) indicated that all the protons (4H) in the olefinic region shifted toward the saturated hydrocarbon region.

This saturated ketone, 3.0 g (0.014 mole) was dissolved in 10 ml of methyl alcohol, and 0.2 g of 15% potassium hydroxide aqueous solution was added to that solution. Then, a solution of sodium borohydride prepared by mixing 0.30 g of NaBH$_4$, 0.02 g of potassium hydroxide, 2.0 ml of water and 2.0 ml of methyl alcohol was added to the reaction mixture with stirring at about 40° C. The reaction mixture thus prepared was stirred for additional 3 hours. Then, methyl alcohol was distilled off under reduced pressure from the mixture and the residue was extracted with ether. After the extract was washed twice with water and dried, it was subjected to distillation under reduced pressure to obtain 2.8 g of 1-(5'- or 6'-ethylnorbornan-2'-yl)-2-methylpentan-3-ol in a yield of 89.3%. This product had a boiling point of 120°–121° C./1.5 mmHg and was a viscous liquid having woody odor with green tone.

IR: O—H stretching vibration was observed at 3,400 cm$^{-1}$ and the absorption of the ketone disappeared by reduction.

NMR: (CDCl$_3$) 6.3τ (triplet, 1H); 6.8τ (broad singlet, 1H); 7.5τ (broad singlet, 1H); 7.8–9.3τ (multiplet, 25H).

| Elemental Analysis: (as C$_{15}$H$_{28}$O) | | |
|---|---|---|
|  | C (%) | H (%) |
| Calculated: | 80.4 | 12.5 |
| Found: | 79.8 | 12.3 |

EXAMPLE 27

Preparation of 1-(5'- or 6'-ethylnorbornan-2'-yl)-2-methyl-1-penten-3-ol

The aldol condensation was carried out in a like manner as Example 26 by using 2.1 g (0.014 mole) of a mixture of 5-ethylnorbornyl-2-aldehyde and 6-ethylnorbornyl-2-aldehyde, and diethyl ketone. Concurrent dehydration was allowed to occur to obtain α,β-unsaturated ketone in a yield of 55%. With regard to this product, the existence of the carbonyl group of the α,β-unsaturated ketone was confirmed by IR and NMR analysis, which indicated that the aldol condensation and subsequent dehydration were completed.

Then, 1.5 g (0.007 mole) of this unsaturated ketone was dissolved in a mixture of methyl alcohol and potassium hydroxide. A solution of sodium borohydride prepared by mixing 0.13 g of NaBH$_4$, 0.01 g of potassium hydroxide, 1.0 ml of water and 1.0 ml of methyl alcohol was added to the reaction mixture with stirring at about 40° C. The obtained mixture was stirred for additional 3 hours.

After the reaction was completed, methyl alcohol was distilled off and the residue was sufficiently washed with water and dried and then distilled under reduced pressure to obtain 1.3 g of 1-(5'- or 6'-ethylnorbornan-2'-yl)-2-methyl-1-penten-3-ol in a yield of 84%. This reaction product had a boiling point of 124°–126° C./2.0 mmHg and was a colorless oily substance having warm and sweet woody odor.

IR: O—H stretching vibration was observed at 3,400 cm$^{-1}$ and the absorption of the carbonyl groups of α,β-unsaturated ketone at 1,660 cm$^{-1}$ was lost through reduction.

NMR: (CDCl$_3$) 4.7–4.8τ (doublet, 1H); 6.1–6.3τ (triplet, 1H); 8.4τ (singlet, 3H); 7.5–9.3τ (multiplet, 21H).

| Elemental Analysis: (as C$_{15}$H$_{26}$O) | | |
|---|---|---|
|  | C (%) | H (%) |
| Calculated: | 81.1 | 11.7 |
| Found: | 80.6 | 11.4 |

EXAMPLE 28

Preparation of 1-(3'-methyl-5'- or 6'-ethylnorbornan-2'-yl)-2-methylpentan-3-ol

The aldol condensation was carried out in a like manner as Example 26 with 5.0 g (0.030 mole) of a mixture of 3-methyl-5-ethylidenenorbornyl-2-aldehyde and 3-methyl-6-ethylidenenorbornyl-2-aldehyde and diethyl ketone, which was followed by dehydration. Thus, α,β-unsaturated ketone was obtained in a yield of 57% and its structure was confirmed by IR and NMR analysis.

In a 500 ml autoclave were then placed 4.0 g (0.017 mole) of this α,β-unsaturated ketone, 100 ml of ethyl alcohol, and 0.2 g of 5% rhodium-alumina catalyst. After the autoclave was closed up, the contents were allowed to react at about 50° C. under hydrogen pressure of 4 kg/cm² for 6 hours, in which about 150 ml of hydrogen gas was absorbed. After the removal of the catalyst, the ethyl alcohol was distilled off and the residue was distilled under reduced pressure to obtain the above 1-(3'-methyl-5'- or 6'-ethylnorbornan-2'-yl)-2-methylpentan-3-ol having a boiling point of 126°–129° C./2.0 mmHg in a yield of 78.0%. This product was a colorless oily substance having refreshing woody odor.

IR: O—H stretching vibration at 3,400 cm$^{-1}$ was observed and the characteristic absorptions of carbon-carbon double bonds and α,β-unsaturated ketone (C=C at 1,640 cm$^{-1}$ and C=O at 1,660 cm$^{-1}$) were lost by reduction.

NMR: (CDCl₃) 6.3τ (triplet, 1H); 6.8τ (broad singlet, 1H); 7.5–9.4τ (multiplet, 28H).

| Elemental Analysis: (as $C_{16}H_{30}O$) | | |
|---|---|---|
| | C (%) | H (%) |
| Calculated: | 80.7 | 12.6 |
| Found: | 80.4 | 12.5 |

EXAMPLE 29

Preparation of 1-(3',3'-dimethyl-5'- or 6'-ethylnorbornan-2'-yl)-2-methyl-1-penten-3-ol and 1-(3',3'-dimethyl-5'- or 6'-ethylnorbornan-2'-yl)-2-methylpentan-3-ol Aldol condensation and dehydration were carried out with 10.0 g (0.056 mole) of a mixture of 3,3-dimethyl-5-ethylnorbornyl-2-aldehyde and 3,3-dimethyl-6-ethylnorbornyl-2-aldehyde and diethyl ketone, in a like manner as Example 26 to obtain α,β-unsaturated ketone in a yield of 60%. The structure of this ketone was identified by IR and NMR analysis.

The unsaturated ketone, 5.0 (0.020 mole) was reduced by using sodium borohydride in a like manner as Example 27 to obtain 4.3 g of 1-(3',3'-dimethyl-5'- or 6'-ethylnorbornan-2'-yl)-2-methyl-1-penten-3-ol in a yield of 85.3%. This product had a boiling point of 122°–125° C./1.7 mmHg and was a colorless oily substance having flowery woody odor.

IR: O—H stretching vibration at 3,360 cm$^{-1}$ was observed and the absorption (1,660 cm$^{-1}$) of the carbonyl group of α,β-unsaturated ketone was lost by reduction.

NMR: (CDCl₃) 4.7–4.8τ (doublet, 1H); 6.2–6.3τ (triplet, 1H); 8.3τ (singlet, 3H); 7.4–9.4τ (multiplet, 25H).

| Elemental Analysis: (as $C_{17}H_{30}O$) | | |
|---|---|---|
| | C (%) | H (%) |
| Calculated: | 81.6 | 12.7 |
| Found: | 81.2 | 11.7 |

In a 500 ml autoclave were placed 3.0 g (0.012 mole) of the above product, 100 ml of ethyl alcohol and 0.1 g of 5% palladium-carbon catalyst and the autoclave was closed. The contents were reacted at room temperature under hydrogen pressure of 2 kg/cm² and the reaction was stopped when about 270 ml of hydrogen gas was absorbed. The catalyst was removed from the reaction mixture and ethyl alcohol was distilled off. The residue was then distilled under reduced pressure to obtain 2.6 g of 1-(3',3'-dimethyl-5'- or 6'-ethylnorbornan-2'-yl)-2-methylpentan-3-ol in a yield of 86.0%. This product had a boiling point of 121°–124° C./1.3 mmHg and was a colorless oily substance having woody odor with green tone.

IR: O—H stretching vibration at 3,360 cm$^{-1}$ was observed and the absorption of C=C stretching vibration of carbon-carbon double bonds at 1,640 cm$^{-1}$ was lost by the hydrogenation.

NMR: (CDCl₃) 6.1–6.3τ (triplet, 1H); 6.7τ (broad singlet, 1H); 7.5–9.3τ (multiplet, 24H); 9.2τ (singlet, 3H); 9.3τ (singlet, 3H).

| Elemental Analysis: (as $C_{17}H_{32}O$) | | |
|---|---|---|
| | C (%) | H (%) |
| Calculated: | 81.0 | 12.7 |
| Found: | 80.6 | 12.3 |

EXAMPLE 30

Preparation of 1-(5'- or 6'-vinylnorbornan-2'-yl)-2-methyl-1-penten-3-ol

Diethyl ketone, 3.2 g (0.037 mole) was dissolved in 15 ml of methyl alcohol and 0.5 g of 40% sodium hydroxide solution was added thereto. To the mixture, 2.1 g (0.014 mole) of a mixture of 5-vinyl-norbornyl-2-aldehyde and 6-vinylnorbornyl-2-aldehyde was slowly added under reflux.

The aldol condensation was carried out by refluxing this mixture for additional 2 hours. Since dehydration occurred simultaneously, no dehydration process was employed. The reaction mixture was distilled under reduced pressure to obtain α,β-unsaturated ketone in a yield of 59%. In the IR and NMR spectrum analysis of this product, the existence of the carbonyl group of the α,β-unsaturated ketone indicated the completion of the aimed reaction.

Then, 1.5 g (0.007 mole) of this unsaturated ketone was dissolved in a mixture of methyl alcohol and potassium hydroxide. With stirring and heating to about 40° C., a solution of sodium borohydride (NaBH₄ 0.13 g+KOH 0.01 g+water 1.0 ml+methanol 1.0 ml) was added, which was followed by 3 hours' stirring. After the reaction was completed, methyl alcohol was distilled off from the reaction mixture and washed with water and dried. It was then distilled under reduced pressure to obtain 1.3 g of 1-(5'- or 6'-vinylnorbornan-2'-yl)-2-methyl-1-penten-3-ol in a yield of 85%. This product had a boiling point of 110°–113° C./0.8–1.1 mmHg and was a colorless oily substance having warm woody odor.

IR: O—H stretching vibration at 3,400 cm$^{-1}$, C—H stretching vibration of the vinyl group at 3,090 cm$^{-1}$, and C=C stretching vibration of the vinyl group at 1,640 cm$^{-1}$ were observed, while the absorption of the carbonyl group of $\alpha,\beta$-unsaturated ketone at 1,670 cm$^{-1}$ was lost by reduction.

NMR: 3.9–4.6$\tau$ (multiplet, 1H); 4.7–4.8$\tau$ (doublet, 1H); 4.9–5.3$\tau$ (multiplet, 2H); 6.2$\tau$ (triplet, 1H); 8.4$\tau$ (singlet, 3H); 9.1–9.3$\tau$ (triplet, 3H); 7.5–9.1$\tau$ (multiplet, 13H).

| Elemental Analysis: (as $C_{15}H_{24}O$) | | |
| --- | --- | --- |
| | C (%) | H (%) |
| Calculated: | 81.8 | 10.9 |
| Found: | 81.4 | 10.8 |

EXAMPLE 31

Preparation of 1-(5'- or 6'-ethylidenenorbornan-2'-yl)-2-methyl-1-penten-3-ol

To 20 ml of 4.6 g (0.053 mole) diethyl ketone solution in methyl alcohol, 0.7 g of 40% sodium hydroxide solution was added. Then, to the mixture, 3.0 g of a mixture of 5-ethylidenenorbornyl-2-aldehyde and 6-ethylidenenorbornyl-2-aldehyde was added dropwise under reflux. After the dropwise addition was completed, the refluxing was continued for additional 2 hours and methyl alcohol was then distilled off, thereby obtaining $\alpha,\beta$-unsaturated ketone in a yield of 60% through distillation under reduced pressure. By IR and NMR analysis of this product, the existence of the carbonyl group of the $\alpha,\beta$-unsaturated ketone indicated the completion of the aimed reaction.

Then, 3.0 g (0.014 mole) of this $\alpha,\beta$-unsaturated ketone was dissolved in a mixture of methyl alcohol and potassium hydroxide. With stirring and heating to about 40° C., a solution of sodium borohydride (NaBH$_4$ 0.26 g + KOH 0.02 g + water 2.0 ml + methanol 2.0 ml) was added to the above solution and additional stirring was continued for 4 hours. After the reaction was completed, methyl alcohol was distilled off from the reaction mixture and washed with water and dried. It was then distilled under reduced pressure to obtain 1-(5'- or 6'-ethylidenenorbornan-2'-yl)-2-methyl-1-penten-3-ol in a yield of 66%. This product had a boiling point of 114°–116° C./0.8–0.9 mmHg and was a colorless oily substance having favorable woody odor with quite fresh green tone.

IR: O—H stretching vibration at 3,400 cm$^{-1}$, and C—H stretching vibration at 3,090 cm$^{-1}$ and C=C stretching vibration at 1,640 cm$^{-1}$ of ethylidene group were observed but the absorption of the carbonyl group of $\alpha,\beta$-unsaturated ketone at 1,670 cm$^{-1}$ was lost by the reduction.

NMR: 4.4–4.9$\tau$ (multiplet, 1H); 4.7–4.8$\tau$ (doublet, 1H); 6.2$\tau$ (triplet, 1H); 8.3–8.5$\tau$ (triplet, 3H); 8.5$\tau$ (singlet, 3H); 7.4–9.4$\tau$ (multiplet, 15H).

| Elemental Analysis: (as $C_{15}H_{24}O$) | | |
| --- | --- | --- |
| | C (%) | H (%) |
| Calculated: | 81.8 | 10.9 |
| Found: | 81.2 | 10.7 |

EXAMPLE 32

Preparation of 1-(3'-methyl-5'- or 6'-vinylnorbornan-2'-yl)-2-methyl-1-penten-3-ol The preparation was carried out in a like manner as the foregoing Example 30 except that 3-methyl-5- or 6-vinylnorbornyl-2-aldehyde was used in place of the foregoing vinylnorbornyl-2-aldehyde, thereby obtaining $\alpha,\beta$-unsaturated ketone in a yield of 62%. It was then reduced likewise to obtain the above compound, 1-(3'-methyl-5'- or 6'-vinylnorbornan-2'-yl)-2-methyl-1-penten-3-ol in a yield of 82%.

This product had a boiling point of 115°–120° C./1.2 mmHg and was a colorless oily substance having favorable warm woody odor.

IR: O—H stretching vibration at 3,400 cm$^{-1}$, and C—H stretching vibration at 3,090 cm$^{-1}$ and C=C stretching vibration at 1,640 cm$^{-1}$ of the vinyl group were observed but the absorption of the carbonyl group of $\alpha,\beta$-unsaturated ketone at 1,670 cm$^{-1}$ was lost by reduction.

NMR: 3.9–4.5$\tau$ (multiplet, 1H); 4.7–4.8$\tau$ (doublet, 1H); 4.9–5.3$\tau$ (multiplet, 2H); 6.2$\tau$ (triplet, 1H); 8.4$\tau$ (singlet, 3H); 9.0$\tau$ (doublet, 3H); 9.1–9.3$\tau$ (triplet, 3H); 7.4–9.2$\tau$ (multiplet, 12H).

| Elemental Analysis: (as $C_{16}H_{26}O$) | | |
| --- | --- | --- |
| | C (%) | H (%) |
| Calculated: | 82.1 | 11.1 |
| Found: | 81.8 | 11.0 |

EXAMPLE 33

Preparation of 1-(3'-methyl-5'- or 6'-ethylidenenorbornan-2'-yl)-2-methyl-1-penten-3-ol The preparation was carried out in a like manner as the foregoing Example 30 except that 3-methyl-5- or 6-ethylidenenorbornyl-2-aldehyde was used in place of the foregoing vinylnorbornyl-2-aldehyde, thereby obtaining $\alpha,\beta$-unsaturated ketone in a yield of 58%. It was then reduced likewise to obtain the above compound, 1-(3'-methyl-5'- or 6'-ethylidenenorbornan-2'-yl)-2-methyl-1-penten-3-ol in a yield of 85%.

This product had a boiling point of 117°–122° C./1.1 mmHg and was a colorless oily substance having woody odor with vetiver tone.

IR: O—H stretching vibration at 3,400 cm$^{-1}$, and C—H stretching vibration at 3,090 cm$^{-1}$ and C=C stretching vibration at 1,640 cm$^{-1}$ of the ethylidene group were observed but the absorption of the carbonyl group of $\alpha,\beta$-unsaturated ketone at 1,670 cm$^{-1}$ was lost by reduction.

NMR: 4.5–4.9$\tau$ (multiplet, 1H); 4.7–4.8$\tau$ (doublet, 1H); 6.2$\tau$ (triplet, 1H); 8.3–8.5$\tau$ (triplet, 3H); 8.5$\tau$ (singlet, 3H); 9.1$\tau$ (doublet, 3H); 7.3–9.4$\tau$ (multiplet, 14H).

| Elemental Analysis: (as $C_{16}H_{26}O$) | | |
| --- | --- | --- |
| | C (%) | H (%) |
| Calculated: | 82.1 | 11.1 |
| Found: | 82.3 | 10.9 | cl EXAMPLE 34

Preparation of 1-(3',3'-dimethyl-5'- or 6'-ethylidenenorbornan-2'-yl)-2-methyl-1-penten-3-ol The preparation was carried out in a like manner as the foregoing Example 30 except that 3,3-dimethyl-5- or 6-ethylidenenorbornyl-2-aldehyde was used in place of the vinyl norbornyl-2-aldehyde, thereby obtaining α,β-unsaturated ketone in a yield of 64%. It was then reduced likewise to obtain 1-(3',3'-dimethyl-5'- or 6'-ethylidenenorbornan-2'-yl)-2-methyl-1-penten-3-ol in a yield of 78%.

This product had a boiling point of 122°–126° C./0.8 mmHg and was a colorless oily substance having woody odor with fougere tone.

IR: O—H stretching vibration at 3,400 cm$^{-1}$, and C—H stretching vibration at 3,090 cm$^{-1}$ and C=C stretching vibration at 1,640 cm$^{-1}$ of the ethylidene group were observed but the absorption of the carbonyl group of α,β-unsaturated ketone at 1,670 cm$^{-1}$ was lost by reduction.

NMR: 4.4–4.9τ (multiplet, 1H); 4.7–4.8τ (doublet, 1H); 6.2τ (triplet, 1H); 8.3–8.5τ (triplet, 3H); 8.5τ (singlet, 3H); 9.1τ (doublet, 6H); 7.3–9.3τ (multiplet, 13H).

| Elemental Analysis: (as $C_{17}H_{28}O$) | | |
|---|---|---|
| | C (%) | H (%) |
| Calculated: | 82.3 | 11.3 |
| Found: | 82.0 | 11.1 |

EXAMPLE 35

Preparation of 4-(5'- or 6'-vinylnorbornan-2'-yl)-3-methyl-3-buten-2-ol

The preparation was carried out in a like manner as the foregoing Example 30 except that 2.7 g (0.037 mole) of methyl ethyl ketone was used in place of diethyl ketone. Through fractional distillation, the aldol condensation product of α,β-unsaturated ketone, 4-(5'- or 6'-vinyl-norbornan-2'-yl)-3-methyl-3-buten-2-on was obtained in a yield of 35%. Then, the reduction in a like manner as Example 30 afforded 4-(5'- or 6'-vinylnorbornan-2'-yl)-3-methyl-3-buten-2-ol in a yield of 80%.

This product had a boiling point of 103°–106° C./0.9 mmHg and was a colorless oily substance having woody odor with fugere tone.

IR: O—H stretching vibration at 3,400 cm$^{-1}$, and C—H stretching vibration at 3,090 cm$^{-1}$ and C=C stretching vibration at 1,640 cm$^{-1}$ of the vinyl group were observed but the absorption of the carbonyl group of α,β-unsaturated ketone at 1,670 cm$^{-1}$ was lost by reduction.

NMR: 3.9–4.6τ (multiplet, 1H); 4.7–4.8τ (doublet, 1H); 4.9–5.3τ (multiplet, 2H); 6.2τ (quartet, 1H); 8.5τ (singlet, 3H); 9.0τ (doublet, 3H); 7.4–9.1τ (multiplet, 11H).

| Elemental Analysis: (as $C_{14}H_{22}O$) | | |
|---|---|---|
| | C (%) | H (%) |
| Calculated: | 81.6 | 10.7 |
| Found: | 81.4 | 10.6 |

EXAMPLE 36

Preparation of Portugal aldehyde

The ethylnorbornyl-2-aldehyde prepared in Example 1 was formulated in the following composition to provide a Portugal aldehyde.

| | |
|---|---|
| n-Octyl aldehyde | 4.0 g |
| n-Nonyl aldehyde | 9.5 g |
| n-Decyl aldehyde | 13.5 g |
| n-Undecyl aldehyde | 38.5 g |
| Lauryl aldehyde | 19.5 g |
| Nonyl methyl acetaldehyde | 6.0 g |
| Norbornane derivative prepared in Example 1 | 9.0 g |
| Total | 100.0 g |

This Portugal aldehyde is suitable for use in formulating a citrus perfume or an orange flavor.

EXAMPLE 37

Preparation of greenish Portugal aldehyde

In the formulation of Example 36, the ethylnorbornyl-2-aldehyde was replaced by the ethylidenenorbornyl-2-aldehyde prepared in Example 3, to give a greenish Portugal aldehyde. When this Portugal aldehyde is formulated in citrus perfume or chpre perfume, the note is converted more fresh or green.

EXAMPLE 38

Preparation of red rose base perfume

The norbornane derivative prepared in Example 26, 1-(5'- or 6'-ethylnorbornan-2'-yl)-2-methylpentan-3-ol was formulated in the following composition to provide red rose base.

| | |
|---|---|
| β-Phenylethyl alcohol | 40 g |
| Rose absolute | 30 g |
| Benzyl salicylate | 5 g |
| Zdravetz oil | 10 g |
| Ethylene brassylate | 5 g |
| Methyl ionone | 2 g |
| Norbornane derivative prepared in Example 26 | 8 g |
| Total | 100 g |

This base perfume is suitable for use in formulating a floral bouquet perfume in a very sweet rose note. Further, it is generally used as the main ingredient of room interior perfumes and attar of rose.

EXAMPLE 39

Preparation of white rose base perfume

The norbornane derivative prepared in Example 27, 1-(5'- or 6'-ethylnorbornan-2'-yl)-2-methyl-1-penten-3-ol was formulated in the following composition to provide a white rose base.

| | |
|---|---|
| Rhodinol | 30 g |
| β-Phenylethyl alcohol | 15 g |
| Methyl ionone | 15 g |
| Cyclopentadecanolide | 15 g |
| Rose absolute | 15 g |
| Norbornane derivative prepared in Example 27 | 10 g |
| Total | 100 g |

This base perfume is suitable for use in preparing formulated perfumes in refreshing white rose note. In addition, it may be widely used as a perfume ingredient for preparing pastiness and powder cosmetics.

EXAMPLE 40

Preparation of cypre base perfume

The norbornane derivative prepared in Example 28, 1-(3'-methyl-5'- or 6'-ethylnorbornan-2'-yl)-2-methylpentan-3-ol was formulated in the following composition to provide a cypre base.

| | |
|---|---|
| Bergamot oil | 21 g |
| Hydroxycitronellal | 15 g |
| Linalool | 10 g |
| Petitgrain oil | 5 g |
| Patchouli oil | 5 g |
| Methyl ionone | 5 g |
| Lemon oil | 5 g |
| Ethylene brassylate | 4 g |
| Isobornyl acetate | 3 g |
| Vetiveryl acetate | 5 g |
| Cedarwood oil | 7 g |
| Rose absolute | 5 g |
| Jasmin oil | 2 g |
| Norbornane derivative prepared in Example 28 | 3 g |
| Total | 100 g |

This cypre base perfume is suitable for use in preparing hair cosmetics and room interior perfumes.

EXAMPLE 41

Preparation of fougere woody perfume

The norbornane derivative prepared in Example 29, 1-(3',3'-dimethyl-5'- or 6'-ethylnorbornan-2'-yl)-2-methylpentan-3-ol was formulated in the following composition to provide a fougere woody base.

| | |
|---|---|
| Lavender oil | 15 g |
| Isoamyl salicylate | 20 g |
| Coumarin | 3 g |
| Oak moss oil | 6 g |
| Geranium oil | 5 g |
| Bergamot oil | 5 g |
| Petitgrain oil | 5 g |
| Vetiver oil | 6 g |
| Patchouli oil | 5 g |
| t-Butylcyclohexyl acetate | 2 g |
| Cyclohexadecanolide | 2 g |
| Methyl isoeugenol | 3 g |
| α-ionone | 3 g |
| Norbornane derivative prepared in Example 29 | 20 g |
| Total | 100 g |

This fougere woody perfume is quite suitable in preparing cosmetics for men, for example, Eau de cologne.

EXAMPLE 42

Preparation of oriental cypre perfume

The norbornane derivative, 1-(3'-methyl-5'- or 6'-ethylnorbornan-2'-yl)-2-methyl-1-penten-3-ol prepared by reduction of the α,β-unsaturated ketone in Example 28, was formulated in the following composition to provide a base perfume in oriental cypre note.

| | |
|---|---|
| Bergamot oil | 40 g |
| Lemon oil | 10 g |
| Linalool | 6 g |
| Geranium oil | 5 g |
| Patchouli oil | 4 g |
| Ylang-Ylang oil | 3 g |
| Vetiver oil | 3 g |
| Oak moss oil | 3 g |
| β-Phenylethyl alcohol | 3 g |
| Rose absolute | 2 g |
| Musk ambrette | 2 g |
| Jasmone | 1 g |
| Benzoin | 1 g |
| Labdanum resinoid | 1 g |
| The above norbornane derivative | 16 g |
| Total | 100 g |

This perfume gives favorable fragrance but it is dark-colored, so that it is not suitable for cosmetics. It is, however, quite suitable as fragrant ingredient for shoe polish, mosquito-repellent mats, deodorants, insecticides, and the like with markable effect.

EXAMPLE 43

Preparation of sandalwood base perfume

The red rose base perfume prepared in Example 38 and the white rose base perfume prepared in Example 39 were formulated in the following composition to provide a sandalwood base perfume.

| | |
|---|---|
| Sandalwood oil | 60 g |
| Vetiver oil | 10 g |
| Musk ambrette | 5 g |
| Benzyl salicylate | 5 g |
| Phenyl acetate | 2 g |
| Base perfume in Example 38 | 10 g |
| Base perfume in Example 39 | 8 g |
| Total | 100 g |

This base perfume has fantastic sandalwood fragrance and its alcoholic solution can be used for perfuming folding fans. Further, it can be used for preparing room interior deodorant composition.

EXAMPLE 44

Preparation of fougere perfume

The norbornane derivative that was prepared in Example 30 was formulated in the following composition to provide a fougere perfume.

| | |
|---|---|
| Lavender oil | 15 g |
| Geranium oil | 5 g |
| Oak moss oil | 4 g |
| Coumarin | 6 g |
| Patchouli oil | 3 g |
| Cedarwood oil | 20 g |
| Methyl salicylate | 1 g |
| Terpinyl acetate | 13 g |
| Amyl salicylate | 9 g |
| Geraniol | 11 g |
| Musk xylene | 5 g |
| Norbornane derivative prepared in Example 30 | 8 g |
| Total | 100 g |

This perfume can be used as a base perfume for toiletries as well as soaps.

EXAMPLE 45

Preparation of oriental rose perfume

The norbornane derivatives prepared in Examples 30 and 31 were formulated in the following composition to provide an oriental rose perfume.

| | |
|---|---|
| Bulgarian rose oil | 12 g |
| β-Phenylethyl alcohol | 26 g |
| Rhodinyl | 32 g |
| Guaiol acetate | 13 g |
| Norbornane derivative prepared in Example 30 | 10 g |
| Norbornane derivative prepared in Example 31 | 7 g |
| Total | 100 g |

This composition is Persian Gulistan perfume and attar of rose is prepared by diluting it with aqueous alcohol solution. It is solidified with carrageenin gel, and the solid can be used as room fragrance having oriental rose odor.

EXAMPLE 46

Preparation of narcissus perfume (I)

The norbornane derivative prepared in Example 33 was formulated in the following composition to provide a narcissus perfume.

| | |
|---|---|
| Petitgrain oil | 20 g |
| 10% Indole solution in ethanol | 10 g |
| Methyl anthranilate | 4 g |
| Cananga oil | 15 g |
| Benzyl acetate | 12 g |
| α-ionone | 6 g |
| p-Cresylphenyl acetate | 2 g |
| Musk ambrette | 3 g |
| Cedarwood oil | 8 g |
| Benzoin | 6 g |
| 10% Phenylacetaldehyde solution in ethyl alcohol | 1 g |
| Benzylideneacetone | 1 g |
| Linalool | 7 g |
| Jasmone | 1 g |
| Norbornane derivative prepared in Example 33 | 4 g |
| Total | 100 g |

This narcissus perfume gives fresh fragrance and used for preparing perfumes for detergents, bath salts and artificial flower aromatics.

EXAMPLE 47

Preparation of narcissus perfume (II)

In the formula of Example 46, the norbornane derivative prepared in Example 33 was replaced by the norbornane derivative prepared in Example 34, where the narcissus perfume was imparted with fantastic tone.

This composition is suitable for use as odor ingredient for preparing perfumes used in rooms or cars.

What is claimed is:

1. A norbornane derivative having a hydrocarbon side chain which is represented by the following general formula (I)

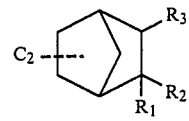

wherein $C_2$ is an ethylidene group or a vinyl group connected to the 5 or 6 position of the norbornane ring, the dashed line connected to $C_2$ is a single bond when $C_2$ is a vinyl group and a double bond when $C_2$ is an ethylidene group, each of $R_1$ and $R_2$ is a hydrogen atom or a methyl group, and $R_3$ is a formyl group or a group represented by the following general formula (II)

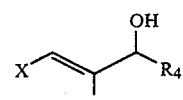

wherein $R_4$ is a methyl group, an ethyl group, a n-propyl group or an isopropyl group and X is a carbon atom of the norbornane ring.

2. A norbornane derivative of claim 1 selected from the group consisting of 4-(5'- or 6'-ethylidene- or 4-(5'- or 6'-vinylnorbornan-2'-yl)-3-methyl-3-buten-2-ol, and their 3'-methyl or 3',3'-dimethyl derivatives.

3. A norbornane derivative of claim 1 selected from the group consisting of 1-(5'- or 6'-ethylidene- or 1-(5'- or 6'-vinyl-norbornan-2'-yl)-2-methyl-1-penten-3-ol, and their 3'-methyl or 3',3'-dimethyl derivatives.

4. A norbornane derivative of claim 1 selected from the group consisting of 1-(5'- or 6'-ethylidene- or 1-(5'- or 6'-vinyl-norbornan-2'-yl)-2,4-dimethyl-1-penten-3-ol, and their 3'-methyl or 3',3'-dimethyl derivatives.

5. A norbornane derivative of claim 1 selected from the group consisting of 1-(5'- or 6'-ethylidene- or 1-(5'- or 6'-vinyl-norbornan-2'-yl)-2-methyl-1-hexen-3-ol, and their 3'-methyl or 3',3'-dimethyl derivatives.

6. A perfume composition containing a compound represented by the following general formula (I)

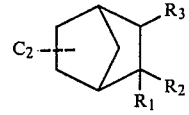

wherein $C_2$ is an ethylidene group or a vinyl group connected to the 5 or 6 position of the norbornane ring, the dashed line connected to $C_2$ is a single bond when $C_2$ is a vinyl group and a double bond when $C_2$ is an ethylidene group, each of $R_1$ and $R_2$ is a hydrogen atom or a methyl group, and $R_3$ is a formyl group or a group represented by the following general formula (II)

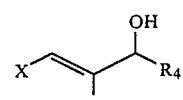

wherein $R_4$ is a methyl group, an ethyl group, a n-propyl group or an isopropyl group and X is a carbon atom of the norbornane ring.

* * * * *